United States Patent [19]

Field et al.

[11] 3,954,753

[45] May 4, 1976

[54] 2-AROYL-3-AMINO PYRAZINES AND THE 3(-2HALOACETAMIDE DERIVATIVES THEREOF

[75] Inventors: George Francis Field, West Caldwell; Leo Henryk Sternbach, Upper Montclair; Armin Walser, West Caldwell, all of N.J.

[73] Assignee: Hoffmann-La Roche Inc., Nutley, N.J.

[22] Filed: Feb. 13, 1975

[21] Appl. No.: 549,566

Related U.S. Application Data

[62] Division of Ser. No. 438,810, Feb. 1, 1974, Pat. No. 3,880,848.

[52] U.S. Cl. .............................. 260/250 BN
[51] Int. Cl.$^2$................................. C07D 241/14
[58] Field of Search ........................ 260/250 BM

[56] References Cited

UNITED STATES PATENTS

| | | | |
|---|---|---|---|
| 2,677,686 | 5/1954 | Smith et al. | 260/250 B |
| 3,240,780 | 3/1966 | Cragoe et al. | 260/250 BM |
| 3,316,266 | 4/1967 | Tull et al. | 260/250 BM |

*Primary Examiner*—Raymond V. Rush
*Assistant Examiner*—D. B. Springer
*Attorney, Agent, or Firm*—Samuel L. Welt; George M. Gould; Frank P. Hoffman

[57] ABSTRACT

Novel pyrazino-1,4-diazepines are disclosed together with processes for their preparation and novel intermediates used in these processes. These novel diazepines are useful as sedatives, muscle-relaxants and anti-convulsants.

2 Claims, No Drawings

2-AROYL-3-AMINO PYRAZINES AND THE 3(-2HALOACETAMIDE DERIVATIVES THEREOF

This is a division, of application Ser. No. 438,810 filed Feb. 1, 1974, now U.S. Pat. No. 3,889,840, issued Apr. 29, 1975.

DETAILED DESCRIPTION OF THE INVENTION

The present invention relates to pyrazino-1,4-diazepines. The invention further comprehends processes for making these novel diazepines and novel intermediates employed in these processes.

More specifically, the compounds of the present invention are selected from the group consisting of compounds of the formula

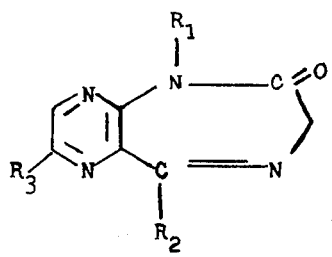

I wherein
$R_1$ is selected from the group consisting of hydrogen, lower alkyl, hydroxy-lower alkyl, lower alkoxy-lower alkyl, cycloalkyl-lower alkyl or di-lower alkylamino-lower alkyl;
$R_2$ signifies phenyl, halophenyl or pyridyl;
$R_3$ signifies hydrogen or halogen and the pharmaceutically acceptable acid addition salts thereof.

As used herein the term "lower alkyl" either alone or in combination refers to straight and branched chain hydrocarbon groups containing from 1 to 7, preferably from 1 to 4 carbon atoms such as for example, methyl, ethyl, propyl, isopropyl, isobutyl, butyl and the like. The term "halogen" refers to all four forms thereof, i.e. bromine, chlorine, fluorine and iodine. The term "lower alkoxy" designates straight or branched chain saturated hydrocarbonoxy groups containing from 1 to 7 carbon atoms preferably 1 to 4 carbon atoms such as methoxy, ethoxy, propoxy and the like. The term "cycloalkyl" refers to cycloalkyl groups containing from 3 to 7 carbon atoms such as cyclopropyl, cyclobutyl, cyclopentyl and the like. The term "halophenyl" refers to mono-halophenyl groups such as chlorophenyl, fluorophenyl and the like and to di-halophenyl groups such as 2,6-dichlorophenyl, 2,6-difluorophenyl and the like.

Preferred among the compounds falling within the scope of formula I above are those wherein $R_2$ signifies pyridyl, i.e. compounds of the formula

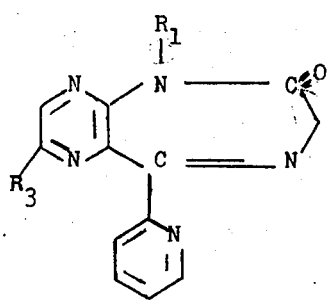

Ia wherein $R_1$ and $R_3$ are as described above and the pharmaceutically acceptable acid addition salts thereof.

Also preferred among the compounds of formula I above are those wherein $R_2$ signifies phenyl or halophenyl, i.e. compounds of the formula

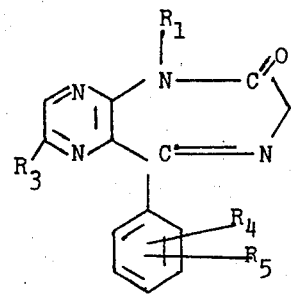

Ib wherein $R_4$ and $R_5$ are each individually hydrogen or halogen and $R_1$ and $R_3$ are as described above and the pharmaceutically acceptable acid addition salts thereof.

When the $R_1$ substituent signifies lower alkyl, methyl is preferred; when $R_1$ signifies hydroxy lower alkyl, hydroxyethyl is preferred; when $R_1$ signifies lower alkoxy-lower alkyl, methoxymethyl is preferred; when $R_1$ signifies cycloalkyl-lower alkyl, cyclopropylmethyl is preferred and when $R_1$ signifies di-lower alkylamino-lower alkyl, diethylamino ethyl is preferred. When $R_2$ is a mono-halophenyl group, the halogen group is preferably chlorine or fluorine and is located at the ortho-position of the 5-phenyl ring. When $R_2$ is a di-halophenyl group, the halogen groups are preferably chlorine or fluorine and are located in the 2-and 6-positions of the 5-phenyl ring.

Representative of the compounds of formula I above are:

1,3-dihydro-5-phenylpyrazino[2,3-f]1,4-diazepin-2(2H)-one;
7-chloro-1,3-dihydro-5-phenylpyrazino[2,3-f]1,4-diazepin-2(2H)-one;
7-bromo-1,3-dihydro-5-pyridylpyrazino[2,3-f]1,4-diazepin-2(2H)-one;
7-chloro-1,3-dihydro-1-methyl-5-phenyl-pyrazino[2,3-f]1,4-diazepin-2-one; and
7-chloro-5-orthofluorophenyl-1,3-dihydro-1-methyl-pyrazino-[2,3-f]1,4-diazepin-2(2H)-one.

The compounds of formula I above are prepared by reacting a compound of the formula

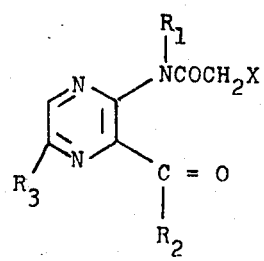

II wherein $R_1 - R_3$ are as described above and X signifies halogen with ammonia.

Treatment of the compounds of formula II above with ammonia results in the formation of the open amine intermediate of the formula

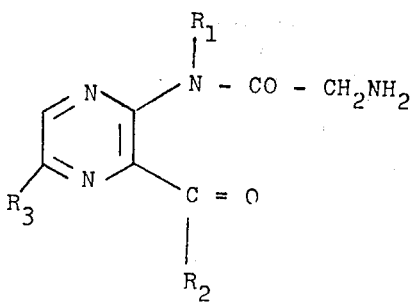

III wherein $R_1 - R_3$ are as described above.

The compound of formula III is preferably not isolated but can be cyclized in situ under the reaction conditions employed to pass directly to the desired compound of formula I. Alternately, the open compound of formula III can be isolated and then subsequently ring closed to the desired compound of formula I. Suitably the cyclization to the desired end product is readily effected by slight heating of the formula III compound, which is preferably dispersed in an inert organic solvent.

The reaction between the compounds of formula II above and ammonia is expediently effected utilizing a temperature in the range of from about −35° to 100°C, most preferably in the range of from about −35° to 35°C. This reaction may be effected in the presence of an inert organic solvent. Suitable solvents for this purpose include alcohols such as methanol, ethanol and the like, ethers such as ethyl ether, tetrahydrofuran, ethylene glycol, dimethyl ether and the like, chlorinated hydrocarbons such as methylene chloride and the like, and pyridine.

In a further process aspect of the present invention, a lower alkyl, hydroxy-lower alkyl, cycloalkyl-lower alkyl, lower alkoxy-lower alkyl or di-lower alkylaminolower alkyl group can be introduced as the $R_1$ substituent into a compound of formula I above wherein $R_1$ is hydrogen by reacting said compound with a suitable alkylating agent. This alkylation is expediently effected by first preparing the N- sodio derivative of the 1-unsubstituted compound and without isolation reacting said N- sodio derivative with a suitable alkylating agent. Alkylating agents that can be used for the present purposes include alkyl halides, halo-lower alkanols, halo-di-lower alkyl ethers and di-lower alkylaminoalkyl halides. Representative of such alkylating agents are 2-bromoethanol, chloro-di-methyl ether, methyliodide, cyclopropylmethyl chloride and 2-bromoethyl-diethylamine. The N- sodio derivative of the 1-unsubstituted compound can be prepared by treating said compound with a sodium lower alkoxide, such as sodium methoxide or with sodium hydride. This reaction is expediently effected in the presence of an inert organic solvent such as dimethylformamide and aromatic hydrocarbons, such as benzene, toluene and the like. Temperatures above and below room temperature may be employed with temperatures from −20°C to room temperature being preferred.

The starting materials of formula II above may be prepared by reacting a benzoyl pyrazine of the formula

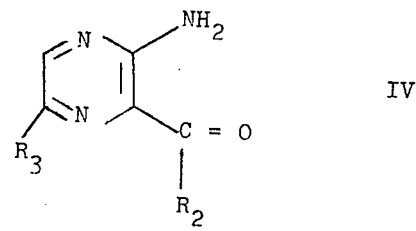

IV wherein $R_2$ and $R_3$ are as described above with a haloacetylhalide. Suitable haloacetylhalides for this purpose include 2-bromoacetylbromide, 2-chloroacetylchloride and the like. Temperature is not critical to this process aspect so that temperatures above and below room temperature can be employed with room temperature being preferred. It is expedient to carry out this reaction in the presence of an inert organic solvent; suitable solvents for this purpose include halogenated hydrocarbons such as methylene chloride and the like.

The benzoyl pyrazine of formula IV above can be prepared following a variety of synthetic approaches. One such synthetic approach is depicted in the following reaction scheme.

REACTION SCHEME I

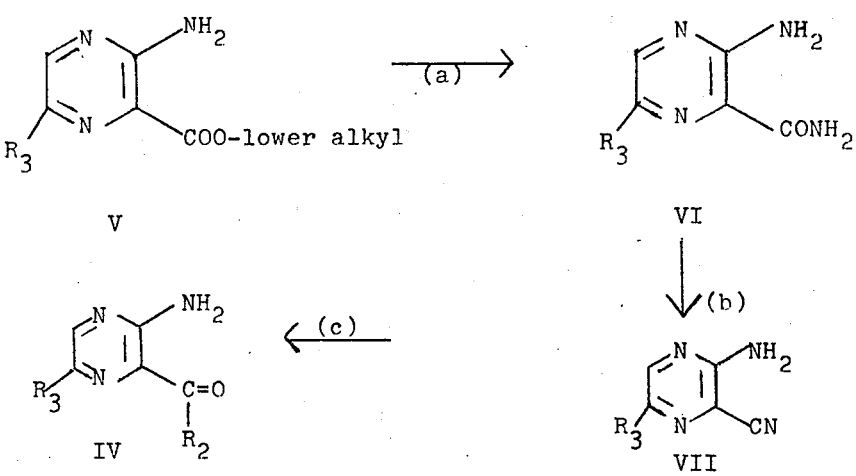

alkylating agent. This alkylation is expediently effected by first preparing the N- sodio derivative of the 1-unsubstituted compound and without isolation reacting said N- sodio derivative with a suitable alkylating agent. Alkylating agents that can be used for the present purposes include alkyl halides, halo-lower alkanols, halo-di-lower alkyl ethers and di-lower alkylaminoalkyl halides. Representative of such alkylating agents are 2-bromoethanol, chloro-di-methyl ether, methyliodide, In Reaction Scheme I shown above, the $R_2$ and $R_3$ substituents are as defined above. The compounds of formula V used as starting materials in this process aspect are known compounds or can be prepared in analogy to the preparation of the known materials. In process step (a) of Reaction Scheme I, the ester of formula V is reacted with ammonia to yield the corresponding amide of formula VI. This reaction is preferably effected in the presence of an inert organic solvent. Suitable solvents for this purpose include alcohols such as methanol, ethanol and the like, ethers such as tetrahydrofuran, hydrocarbons such as hexane and the like, dimethylformamide and dimethylsulfoxide. The ammonia treatment of the compound of formula V is preferably effected under pressure and at elevated temperatures, most preferably at temperatures between 60° and 150°C.

Process step (b) in Reaction Scheme I above involves the dehydration of the amide of formula VI to the corresponding cyanide compound of formula VII. This dehydration is carried out employing conventional dehydrating agents such as thionyl chloride, phosphorous pentoxide and the like. It is expedient to perform this reaction in the presence of an inert organic solvent; suitable solvents include hydrocarbons such as hexane and the like, pyridine, chlorinated hydrocarbons such as methylene chloride, chloroform and the like. Temperature is not critical to this process aspect so that temperatures between room temperature and the re-

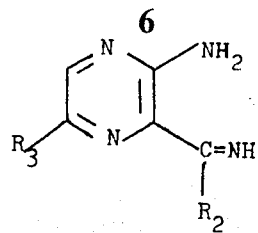

wherein $R_2$ and $R_3$ are as described above.

This imine intermediate need not be isolated, but is hydrolyzed to the ketone of formula IV, for example by the addition of dilute hydrochloric acid to the reaction mixture during the work-up.

Alternately, the starting material of formula IV above may be prepared following the synthetic approach outlined in Reaction Scheme II which follows.

REACTION SCHEME II

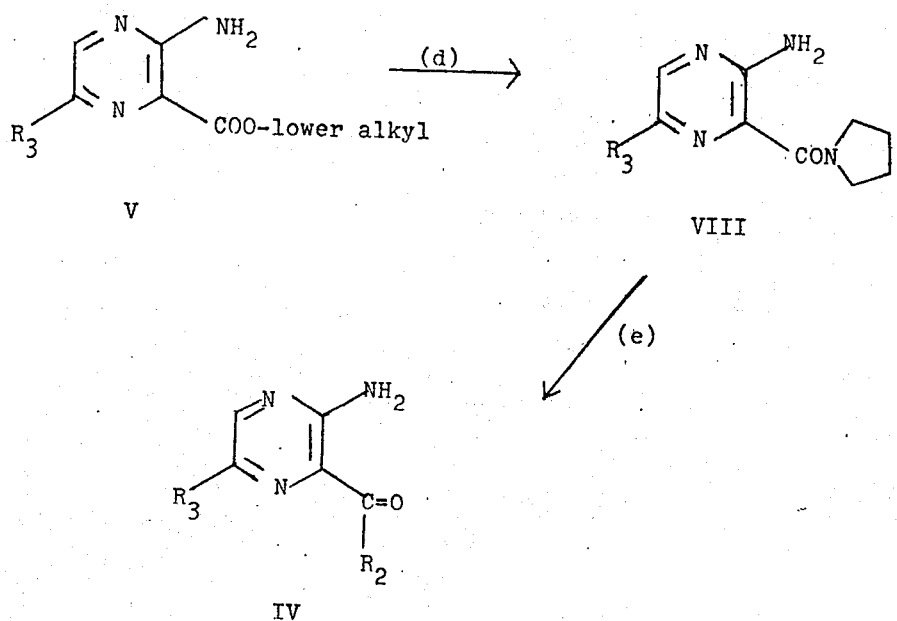

flux temperature of the reaction medium can be employed with the reflux temperature being preferred.

Process step (c) in Reaction Scheme I above involves the reaction of an arylorganometallic reagent with the cyanide compound of formula VII to introduce the desired $R_2$ substituent. Suitable arylorganometallic reagents for the present purposes include phenyl lithium, pyridyl lithium, phenyl magnesium bromide, orthochlorophenylmagnesium bromide, 2,6-difluorophenyl(lithium) and the like. The reaction between the cyanide compound of formula VII and the arylorganometallic reagent is preferably effected in the presence of an inert organic solvent. Suitable solvents include ethers, such as tetrahydrofuran and hydrocarbons such as hexane and the like. Temperature is not critical to this process aspect so that temperatures below or above room temperature can be employed with room temperature being preferred. During the Grignard reaction, there is first formed the imine intermediate of the formula In process step (d) in Reaction Scheme II above, the ester of formula V is reacted with a secondary amine. Reaction Scheme II illustrates one such reaction in that the ester of formula V is reacted with pyrrolidine to yield the pyrrolidide derivative of formula VIII. However, other suitable secondary amines for the present purposes include dimethylamine, diethylamine, piperidine, morphine and the like. The reaction of the ester of formula V with a secondary amine can be effected with or without the use of a solvent system, depending mainly on the nature of the secondary amine employed. If a solvent system is employed, suitable solvents include alcohols such as methanol, ethanol and the like, ethers such as tetrahydrofuran, hydrocarbons such as hexane and the like, dimethylsulfoxide and dimethylformamide. The desired benzoylpyrazine of formula IV can then be prepared by treating the resulting tertiary amide from process step (d) with the appropriate arylorganometallic reagent. The reaction conditions and the reagents discussed for process step (c) of Reaction Scheme I can also be employed in process step (e) of Reaction Scheme II.

The compounds of formulae IV and VIII are novel and as such form a part of the present invention.

The compounds of formula I above form pharmaceutically acceptable acid addition salts with organic and inorganic acids. Thus the compounds of the present invention form pharmaceutically acceptable acid addition salts with inorganic acids such as the hydrohalic acids, for example hydrochloric acid and hydrobromic acid, and with organic acids such as tartaric acid, citric acid, camphor sulfonic acid, ethane sulfonic acid, toluene sulfonic acid, salicylic acid, ascorbic acid, maleic acid, succinic acid, formic acid, acetic acid and the like.

The compounds of formula I above as well as their pharmaceutically acceptable acid addition salts are useful as anticonvulsant, muscle relaxant and sedative agents. Thus, the compounds of the present invention and their pharmaceutically acceptable salts can be used as medicaments. For example, they can be used in the form of pharmaceutical preparations which contain them or their salts in ad-mixture with a pharmaceutical organic or inorganic carrier material which is suitable for enteral or parenteral application such as, for example, water, gelatin, lactose, starches, magnesium sterate, talc, vegetable oils, gum arabic, polyalkyleneglycols, vaseline, etc. The pharmaceutical preparations can be prepared in solid form (e.g. as tablets, dragees, suppositories, capsules) or in liquid form (e.g. as solutions, suspensions or emulsions). They may be sterilized and/or contain additives such as preserving, stabilizing, wetting or emulsifying agents, salts for varying the osmotic pressure or buffers. They can also contain other therapeutically valuable substances.

The compounds of formula I above or their pharmaceutically acceptable salts can be administered at dosages adjusted to individual requirements and fitted to the pharmaceutical exigencies of the situation. Convenient pharmaceutical dosages are in the range of from about 2 mg. to about 200 mg. per day.

The useful anticonvulsant activity of the compounds of formula I above is shown in warm blooded animals utilizing the standard antimetrazole test. This test was carried out according to the method of Everett and Richard (J. P. E. T., 81: 402, 1944). The $ED_{50}$ was calculated as the dose which would prevent convulsions in 50% of the mice tested after administration of 125 mg/kg of pentylenetetrazole by the subcutaneous route. Following these test procedures 7-chloro-1,3-dihydro-5-phenyl pyrazino[2,3-f] 1,4-diazepin-2(2H)-one (Compound A) shows an $ED_{50}$ of $18.0 + 4.0$ mg/kg, indicating that this compound exhibits anti-convulsant activity.

The sedative and muscle relaxant activity of the compounds of formula I above are shown using the standard foot shock test. In this test a pair of mice is confined under a 1 liter beaker placed on a grid which presents shock to the feet. At least five fighting episodes are elicited in a two minute period. Pairs of mice are marked and pretreated 1 hour prior to a second shock. Logarithmic dose intervals are utilized up to a maximum of 100 mg/kg. At the 100% blocking dose, three out of three pairs must be blocked from fighting. The measurements are made at the dose level at which 100% blocking is observed and the results are expressed as the dose in mg/kg ($PD_{50}$) which blocks the fighting response for 1-hour. Following these test procedures, compound A exhibited a $PD_{50}$ of 50 mg/kg, indicating that this compound exhibits sedative and muscle-relaxant activity.

The following examples are illustrative of the present invention. All temperatures are given in degrees Centigrade.

Example 1

Preparation of 2-aminopyrazine-3-carboxylic acid pyrrolidide

A solution of 10 g. (0.065 mol) of methyl 2-aminopyrazine-3-carboxylate in 100 ml. of methanol and 25 ml. of pyrrolidine was refluxed for 18 hours. The residue obtained after evaporation under reduced pressure was triturated with ether to yield 8.8 g. (70%) of the above-named product as yellow crystals, with m.p. 100°–105°. A second crop of 2.3 g. (18%) with m.p. 95°–105° was obtained from the mother liquors. The analytical sample was recrystallized from 2-propanol. The pale yellow prisms had a melting point of 104°–106°.

Example 2

Preparation of 2-amino-5-chloropyrazine-3-carboxylic acid pyrrolidide

Methyl 2-amino-5-chloropyrazine-3-carboxylate was treated as described in Example 1 with 25 ml. of pyrrolidine in 100 ml. of methanol. Crystallization from ether yielded 7 g. (72%) of the above-named product with m.p. 90°–95°. Recrystallization from 2-propanol gave pale yellow needles with m.p. 95°–97°.

Example 3

Preparation of 2-amino-3-benzoylpyrazine

A. 2-Amino-3-cyanopyrazine (2.4 g. or 0.02 mol) was added to a freshly prepared solution of 30.5 g. (0.163 mol) phenylmagnesium bromide in 200 ml. tetrahydrofuran. After stirring and refluxing for 18 hours, the reaction mixture was cooled in ice water, hydrolyzed by addition of 400 ml. of water and acidified to pH ~ 2 by addition of 3N hydrochloric acid. The two-phase system was stirred at room temperature for 30 minutes and was then made alkaline by addition of sodium hydroxide.

The organic layer was separated and dried over alumina. The oil obtained after filtration and evaporation was crystallized from methylene chloride/petroleum ether to yield 1.1 g. (27.5%) of the above-named product as yellow prisms, m.p. 155°–157° after recrystallization from ethyl acetate.

B. 2-Aminopyrazine-3-carboxylic acid pyrrolidide (63.4 g. or 0.33 mol) was added to a solution of freshly prepared phenylmagnesium bromide (305 g.) in 1 l. of tetrahydrofuran while the temperature was kept at 20°–30° by cooling with an ice bath. After stirring at room temperature for 2 hours, the mixture was hydrolyzed by addition of 2 l. of water. The aqueous layer was extracted twice with 500 ml. of methylene chloride. The extracts were combined with the organic layer, dried over sodium sulfate and evaporated. The brown residue was slurried with ether to yield 37.5 g. (56%) of yellow crystals of the above-named product.

Example 4

Preparation of 2-amino-3-benzoyl-5-chloropyrazine

2-Amino-5-chloropyrazine-3-carboxylic acid pyrrolidide (9 g. or 0.04 mol) was added to a freshly prepared solution of 36.2 g. (0.2 mol) of phenylmagnesium bromide in 300 ml. of tetrahydrofuran cooled to 20°. After addition, the reaction mixture was stirred for 3 hours at room temperature and was then hydrolyzed by addition of 150 ml. of water. The organic layer was separated, dried over alumina, filtered and evaporated. Crystallization of the oil obtained from ether yielded 2 g. (50%) of the above-named product as yellow crystals, m.p. 158°–161°. The analytical sample was recrystallized from ethyl acetate, m.p. 160°–161°.

Example 5

Preparation of 3-benzoyl-2-(2-bromoacetamido)pyrazine

A solution of 2 g. (0.01 mol) of 2-amino-3-benzoyl-pyrazine and 20.2 g. (0.1 mol) of 2-bromo-acetyl bromide in 50 ml. of methylene chloride was layered with 25 ml. of 10% aqueous sodium carbonate solution. The two-phase mixture was stirred for 1 hour at room temperature. The methylene chloride layer was separated, washed several times with 10% aqueous sodium carbonate solution and was dried over sodium sulfate. The residue obtained after evaporation was crystallized from methylene chloride/hexane to yield 2.9 g. (90.6%) of the above-named product as tan crystals, m.p. 130°–135° dec.

Example 6

Preparation of 3-benzoyl-3-(2-bromoacetamido)-5-chloropyrazine

2-Amino-3-benzoyl-5-chloropyrazine (0.9 g or 4 mmol) was reacted as described in Example 5 with 8.1 g. (0.04 mol) of 2-bromoacetyl bromide in 25 ml. methylene chloride and 25 ml. of 10% aqueous sodium carbonate solution. The same work up yielded 1 g. (71%) of the above-named product with a melting point of 120°–125° dec. Recrystallization from methylene chloride/petroleum ether afforded colorless needles with a melting point of 124°–126° dec.

Example 7

Preparation of 1,3-dihydro-5-phenylpyrazino[2,3-f]1,4-diazepin-2(2H)-one.

A slow stream of anhydrous ammonia was introduced into a solution of 2.9 g. (9 mmol) of 3-benzoyl-2-(2-bromoacetamido) pyrazine in 70 ml. of ethyl acetate and 50 ml. of methylene chloride. After three hours, the introduction of ammonia was stopped and the mixture was stirred overnight at room temperature. The precipitated salt was removed by filtration. The filtrate was evaporated and the residue crystallized from methylene chloride/ethyl acetate to give the above-named product as tan crystals, m.p. 193°–198° dec. Recrystallization from ethyl acetate/methylene chloride and treatment with charcoal yielded off-white product with m.p. 213°–215° dec.

Example 8

Preparation of 7-chloro-1,3-dihydro-5-phenylpyrazino[2,3-f]1,4-diazepin-2(2H)-one A slow stream of anhydrous ammonia was introduced for 6 hours into a solution of 4.5 g. (0.013 mol) of 3-benzoyl-2-(2-bromoacetamido)-5-chloropyrazine in 100 ml. of ethyl acetate and 50 ml. of methylene chloride. The crude product obtained after filtration and evaporation was purified by chromatography on silica gel. Elution with 20% ethyl acetate in methylene chloride yielded two compounds, first, 2-amino-3-benzoyl-5-chloropyrazine and second, 7-chloro-1,3-dihydro-5-phenylpyrazino[2,3-f]1,4-diazepin-2(2H)-one with m.p. 223°–226° dec.

Example 9

Preparation of 7-chloro-1,3-dihydro-1-methyl-5-phenyl-2H-pyrazino[2,3-f][1,4]diazepin-2-one Dimethylsulfate, 1.15g (9mmol), was added to a solution of 1.2g (4.4mmol) of 7-chloro-1,3-dihydro-5-phenyl-2H-pyrazino[2,3-f] [1,4] diazepin-2-one and 1g (9mmol) of potassium t-butoxide in 30 ml of ethanol. After stirring for 10 min at room temperature, the reaction mixture was diluted with 10% aqueous sodium carbonate solution and was extracted with methylene chloride. The extracts were washed with water, dried over sodiumsulfate and evaporated. The residue was chromatographed over 40g of silica gel (Merck, 70–230 mesh) using 10% ethylacetate in methylene chloride. The combined clean fractions were evaporated and the residue was crystallized from ether/hexane to yield the above-named product, with mp. 105°–107°.

| Example 10 Capsule Formulation | Per Capsule |
|---|---|
| 7-Chloro-1,3-dihydro-5-phenylpyrazino [2,3-f]1,4-diazepin-2(2H)-one | 50 mg |
| Lactose, USP | 125 mg |
| Corn Starch, USP | 30 mg |
| Talc, USP | 5 mg |
| Total Weight | 210 mg |

Procedure
1. The drug was mixed with lactose and corn starch in a suitable mixer.
2. The mixture was further blended by passing through a Fitzpatrick Comminuting machine with a No. 1A screen with knives forward.
3. The blended powder was returned to the mixer, the talc added and blended thoroughly.
4. The mixture was filled into No. 4 hard shell gelatin capsules on a Parke Davis capsulating machine.

| Example 11 Capsule Formulation | Per Capsule |
|---|---|
| 7-Chloro-1,3-dihydro-5-phenylpyrazino [2,3-f]1,4-diazepin-2(2H)-one | 10 mg |
| Lactose | 158 mg |
| Corn Starch | 37 mg |
| Talc | 5 mg |
| Total Weight | 210 mg |

Procedure
1. The drug was mixed with the lactose and corn starch in a suitable mixer.
2. The mixer was further blended by passing through a Fitzpatrick Comminuting machine with a No. 1A screen with knives forward.
3. The blended powder was returned to the mixer, the talc added and blended thoroughly. The mixture was then filled into No. 4 hard shell gelatin capsules on a Parke Davis capsulating machine. (Anysimilar type machine may be used).

| Example 12 Tablet Formulation | Per Tablet |
|---|---|
| 7-Chloro-1,3-dihydro-5-phenylpyrazino [2,3-f]1,4-diazepin-2(2H)-one | 25.00 mg |
| Lactose, USP | 64.50 mg |
| Corn Starch | 10.00 mg |
| Magnesium Stearate | 0.50 mg |
| Total Weight | 100.00 mg |

Procedure
1. The drug was mixed with the lactose, corn starch and magnesium stearate in a suitable mixer.
2. The mixture was further blended by passing through a Fitzpatrick Comminuting machine fitted with a No. 1A screen with knives forward.
3. The mixed powders were slugged on a tablet compressing machine.
4. The slugs were comminuted to a mesh size (No. 16 screen) and mixed well.
5. The tablets were compressed at a tablet weight of 100 mg using tablet punches having a diameter of approximately ¼ inch. (Tablets may be either flat or biconvex and may be scored if desired).

| Example 13 Tablet Formulation | Per Tablet |
|---|---|
| 7-Chloro-1,3-dihydro-5-phenylpyrazino [2,3-f]1,4-diazepin-2(2H)-one | 10.0 mg |
| Lactose | 113.5 mg |
| Corn Starch | 70.5 mg |
| Pregelatinized Corn Starch | 8.0 mg |
| Calcium Stearate | 3.0 mg |
| Total Weight | 205.0 mg |

Procedure
1. The drug was mixed with the lactose, corn starch and pregelatinized corn starch in a suitable size mixer.
2. The mix was passed through a Fitzpatrick Comminuting machine fitted with No. 1A screen and with knives forward.
3. The mix was returned to the mixer and moistened with water to a thick paste. The moist mass was passed through a No. 12 screen and the moist granules were dried on paper lined trays at 110°F.
4. The dried granules were returned to the mixer, the calcium stearate was added, and mixed well.
5. The granules were compressed at a tablet weight of 200 mg using standard concave punches having a diameter of five-sixteenths inch.

We claim:
1. A compound of the formula

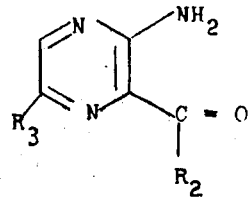

wherein $R_2$ signifies phenyl, halophenyl or pyridyl and $R_3$ signifies hydrogen or halogen.

2. A compound of the formula

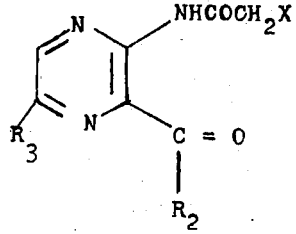

wherein X signifies halogen, $R_2$ signifies phenyl, halophenyl or pyridyl and $R_3$ signifies hydrogen or halogen.

* * * * *